US012808885B2

(12) United States Patent
Chiu

(10) Patent No.: US 12,808,885 B2
(45) Date of Patent: Nov. 24, 2026

(54) METHODS AND KITS FOR DIAGNOSING MILD COGNITIVE IMPAIRMENT

(71) Applicant: Far Eastern Memorial Hospital, New Taipei City (TW)

(72) Inventor: Yen-Ling Chiu, New Taipei City (TW)

(73) Assignee: FAR EASTERN MEMORIAL HOSPITAL, New Taipei City (TW)

( * ) Notice: Subject to any disclaimer, the term of this patent is extended or adjusted under 35 U.S.C. 154(b) by 402 days.

(21) Appl. No.: 17/812,916

(22) Filed: Jul. 15, 2022

(65) Prior Publication Data

US 2023/0025293 A1 Jan. 26, 2023

Related U.S. Application Data

(60) Provisional application No. 63/222,463, filed on Jul. 16, 2021.

(51) Int. Cl.
*G01N 33/68* (2006.01)

(52) U.S. Cl.
CPC ... *G01N 33/6896* (2013.01); *G01N 2333/525* (2013.01); *G01N 2333/55* (2013.01); *G01N 2333/57* (2013.01); *G01N 2333/70575* (2013.01); *G01N 2333/70596* (2013.01); *G01N 2800/2814* (2013.01); *G01N 2800/52* (2013.01)

(58) Field of Classification Search
CPC ..... G01N 33/6896; G01N 2333/70596; G01N 33/505; G01N 2333/525; G01N 2333/57; G01N 2800/52; G01N 2333/55; G01N 2333/70575; G01N 2800/2814
See application file for complete search history.

(56) References Cited

U.S. PATENT DOCUMENTS

2003/0077261 A1* 4/2003 Paris ....................... A61P 19/02
514/19.3

OTHER PUBLICATIONS

Neelapu, S., et al., "Chimeric antigen receptor T-cell therapy—assessment and management of toxicities", Nat Rev Clin Oncol, 2018, (15)47-62 (Year: 2018).*
Ramalingam, S. et al., "Phase I and Pharmacokinetic Study ofVorinostat, A Histone Deacetylase Inhibitor, in Combinationwith Carboplatin and Paclitaxel forAdvanced Solid Malignancies", Clin Cancer Res, 2007, 13(12) (Year: 2007).*
BioTechne-Tocris, Certificate of Analysis, Amyloid Beta-peptide (1-42, human), Cat No. 1428, XAS No. 107761-42-2 (Year: 2024).*
International Search Report and Written Opinion issued in PCT/US22/73799, dated Jan. 23, 2023, 26 pages provided.
Sudhanshu Agrawal et al., "IgM response against amyloid-beta in aging: a potential peripheral protective mechanism", Alzheimers Research & Therapy, 2018, vol. 10 No. 81, pp. 1-11.

* cited by examiner

*Primary Examiner* — Olga N Chernyshev
(74) *Attorney, Agent, or Firm* — HSML P.C.

(57) ABSTRACT

Provided is a method for diagnosing a subject having or at risk of having mild cognitive impairment (MCI), including stimulating T cells in a biological sample obtained from the subject with an amyloid β peptide or a fragment thereof and evaluating a magnitude of a T cell response toward the amyloid β peptide or the fragment thereof. Also provided is a kit for diagnosing MCI by using the method.

12 Claims, 10 Drawing Sheets

Specification includes a Sequence Listing.

SEQUENCE LISTING

```
Sequence total quantity: 12
SEQ ID NO: 1             moltype = AA  length = 42
FEATURE                  Location/Qualifiers
REGION                   1..42
                         note = peptide
source                   1..42
                         mol_type = protein
                         organism = synthetic construct
SEQUENCE: 1
DAEFRHDSGY EVHHQKLVFF GEDVGSNKGA IIGLMVGGVV IA                        42

SEQ ID NO: 2             moltype = AA  length = 15
FEATURE                  Location/Qualifiers
REGION                   1..15
                         note = peptide
source                   1..15
                         mol_type = protein
                         organism = synthetic construct
SEQUENCE: 2
DAEFRHDSGY EVHHQ                                                      15

SEQ ID NO: 3             moltype = AA  length = 15
FEATURE                  Location/Qualifiers
REGION                   1..15
                         note = peptide
source                   1..15
                         mol_type = protein
                         organism = synthetic construct
SEQUENCE: 3
FRHDSGYEVH HQKLV                                                      15

SEQ ID NO: 4             moltype = AA  length = 15
FEATURE                  Location/Qualifiers
REGION                   1..15
                         note = peptide
source                   1..15
                         mol_type = protein
                         organism = synthetic construct
SEQUENCE: 4
DSGYEVHHQK LVFFG                                                      15

SEQ ID NO: 5             moltype = AA  length = 15
FEATURE                  Location/Qualifiers
REGION                   1..15
                         note = peptide
source                   1..15
                         mol_type = protein
                         organism = synthetic construct
SEQUENCE: 5
YEVHHQKLVF FGEDV                                                      15

SEQ ID NO: 6             moltype = AA  length = 15
FEATURE                  Location/Qualifiers
REGION                   1..15
                         note = peptide
source                   1..15
                         mol_type = protein
                         organism = synthetic construct
SEQUENCE: 6
HHQKLVFFGE DVGSN                                                      15

SEQ ID NO: 7             moltype = AA  length = 15
```

-continued

```
FEATURE                 Location/Qualifiers
REGION                  1..15
                        note = peptide
source                  1..15
                        mol_type = protein
                        organism = synthetic construct
SEQUENCE: 7
KLVFFGEDVG SNKGA                                                    15

SEQ ID NO: 8            moltype = AA  length = 15
FEATURE                 Location/Qualifiers
REGION                  1..15
                        note = peptide
source                  1..15
                        mol_type = protein
                        organism = synthetic construct
SEQUENCE: 8
FFGEDVGSNK GAIIG                                                    15

SEQ ID NO: 9            moltype = AA  length = 15
FEATURE                 Location/Qualifiers
REGION                  1..15
                        note = peptide
source                  1..15
                        mol_type = protein
                        organism = synthetic construct
SEQUENCE: 9
EDVGSNKGAI IGLMV                                                    15

SEQ ID NO: 10           moltype = AA  length = 15
FEATURE                 Location/Qualifiers
REGION                  1..15
                        note = peptide
source                  1..15
                        mol_type = protein
                        organism = synthetic construct
SEQUENCE: 10
GSNKGAIIGL MVGGV                                                    15

SEQ ID NO: 11           moltype = AA  length = 15
FEATURE                 Location/Qualifiers
REGION                  1..15
                        note = peptide
source                  1..15
                        mol_type = protein
                        organism = synthetic construct
SEQUENCE: 11
KGAIIGLMVG GVVIA                                                    15

SEQ ID NO: 12           moltype = AA  length = 42
FEATURE                 Location/Qualifiers
REGION                  1..42
                        note = peptide
source                  1..42
                        mol_type = protein
                        organism = synthetic construct
SEQUENCE: 12
DAEFRHDSGY EVHHQKLVFF AEDVGSNKGA IIGLMVGGVV IA                      42
```

METHODS AND KITS FOR DIAGNOSING MILD COGNITIVE IMPAIRMENT

BACKGROUND

1. Technical Field

The present disclosure relates to diagnostic assays to identify subjects with mild cognitive impairment (MCI), and particularly to methods and kits for diagnosing subjects having or at risk of having MCI by evaluating an amyloid-specific T cell response.

2. Description of Related Art

Neurodegenerative diseases occurs when neuron function progressively attenuates. As neuron function deteriorates over time, an individual may start to have mild problems with coordination, such as activities related to talking, balance, movement, etc. Degenerative diseases may not be apparent until a part of the nerve cells lose function and die ultimately. Conditions and disorders in neurodegenerative diseases are diverse and heterogeneous. Depending on the type of the neurodegenerative diseases, such conditions and disorders may be a threat of life and impact living seriously. Examples of neurodegenerative diseases includes Alzheimer's disease, Parkinson's disease, amyotrophic lateral sclerosis (ALS), Friedreich ataxia, Huntington's disease, Lewy body disease, and spinal muscular atrophy.

Some neurodegenerative diseases are associated with amyloid family, including Alzheimer's disease, Parkinson's disease, amyotrophic lateral sclerosis (ALS), and multiple sclerosis (MS). Take Alzheimer's disease (AD) for an example, AD is characterized by the accumulation of the β-amyloid protein (amyloid β) within the brain. With population aging, the burgeoning global increase in the number of people with dementia from around 26 million in 2005 to over 80 million by 2040 presents a public health challenge of unprecedented magnitude[1].

Converging evidence from both genetic at-risk cohorts and clinically normal elder individuals suggests that the underlying pathology for Alzheimer's disease (AD), the most common form of dementia, likely begins years before the onset of disease[2]. Mild cognitive impairment (MCI) has come to be recognized as an intermediate state of subclinical impairment whereby individuals may have cognitive symptoms of a mild nature but generally continue to function virtually normally in the community[3-5]. Current data indicate that individuals with MCI are at an increased risk of progression to dementia, with a conversion rate of approximately 10% to 15% per year[3,5]. Therefore, recognizing as early as possible the presence of impairment in cognitive functioning is becoming a crucial issue.

Besides the accumulation of extracellular amyloid β (Aβ) plaques, other neuropathological features seen in the post-mortem brains of AD patients are generalized cortical atrophy, neuronal and synaptic loss, and intracellular neurofibrillary tangles (NFTs) consisting of hyperphosphorylated tau[6]. Neuroimaging presents an invaluable opportunity for developing reliable AD biomarkers, enabling neuropathological features to be visualized, either directly or indirectly, in the living brain. This is illustrated in the use of amyloid-labeling positron emission tomography (PET) tracers to quantify amyloid plaques in vivo, which correlates strongly with in vitro measures of amyloid burden in post-mortem AD brains[7].

Approximately 50% to 70% of patients with MCI showed significant cortical amyloid PET retention with intermediate levels compared to AD patients and normal controls[8,9]. This high amyloid β burden in MCI patients is found to correlate better with lower episodic memory performance [10,11]. Furthermore, in longitudinal studies assessing the effect of Aβ deposition on disease progression, MCI patients with high amyloid PET retention at baseline have a higher rate of progression to AD than those with low Aβ burden, with sensitivity ranging from 83.3% to 100% and specificity from 41.1% to 100%, respectively[12]. Detection of Aβ pathology at the pre-symptomatic stages of AD may help assess the potential effects of Aβ deposition on cognition and/or neurodegeneration and identify individuals that may be most likely to benefit from therapies aimed at reducing or eliminating Aβ from the brain.

However, the practicality of neuroimaging modalities for routine diagnostic purposes is limited because of insufficient sensitivity and specificity, as well as being expensive and labor-intensive. Hence, an unmet need still remains for an additional test and method of efficiently assessing dementia at stages where it is not clinically expressed and in the early stages of its clinical expression.

SUMMARY

In view of the foregoing, the present disclosure provides diagnostic tools involving biomarkers capable of detecting the prodrome condition of the amyloid-related neurodegenerative diseases such as AD, i.e., the early symptom that might indicate the start of an amyloid-related neurodegenerative disease. In at least one embodiment of the present disclosure, a method for diagnosing a subject having or at risk of having mild cognitive impairment (MCI) is provided. The method of the present disclosure comprises: stimulating T cells in a biological sample obtained from the subject with an amyloid β peptide or a fragment thereof; and evaluating a magnitude of a T cell response toward the amyloid β peptide or the fragment thereof.

In at least one embodiment of the present disclosure, the amyloid β peptide or the fragment thereof for use with the method described herein may be derived from the full-length amyloid β protein (Aβ1-42) comprising, consisting of, or consisting essentially of at least a portion of the amino acid sequence DAEFRHDSGYEVHHQKLVFFAEDVGSNKGAIIGLMVGGVVIA (SEQ ID NO. 12). In some embodiments, the amyloid β peptide for use with the method described herein may be derived from the full-length A21G Flemish-type mutant of amyloid β protein comprising, consisting of, or consisting essentially of at least a portion of the amino acid sequence DAEFRHDSGYEVHHQKLVFFGEDVGSNKGAIIGLMVGGVVIA (SEQ ID NO. 1). Nevertheless, it is noted that the amyloid β peptide or the fragment thereof for use with the method described herein may be derived from any full-length wild-type amyloid β protein variants known in the art.

In at least one embodiment of the present disclosure, the fragment of the amyloid β peptide for use with the method described herein may be derived from the full-length sequence set forth in SEQ ID NO. 1 or SEQ ID NO. 12. In some embodiments, the fragment of the amyloid β peptide comprises at least 10 (e.g., 10 to 30, 12 to 25, and 15 to 20) consecutive amino acids of the amino acid sequence of SEQ ID NO. 1 or SEQ ID NO. 12. In some embodiments, the fragment of the amyloid β peptide comprises, consists of, or consists essentially of the amino acid sequence DAEFRHDSGYEVHHQ (Aβ1-15, SEQ ID NO. 2), FRHDSGYEVHHQKLV (Aβ4-18, SEQ ID NO. 3), DSGYEVHHQKLVFFG (Aβ7-21, SEQ ID NO. 4), YEVHHQKLVFFGEDV (Aβ10-24, SEQ ID NO. 5), HHQKLVFFGEDVGSN (Aβ13-27, SEQ ID NO. 6), KLVFFGEDVGSNKGA (Aβ16-30, SEQ ID NO. 7), FFGEDVGSNKGAIIG (Aβ19-33, SEQ ID NO. 8), EDVGSNKGAIIGLMV (Aβ22-36, SEQ ID NO. 9), GSNKGAIIGLMVGGV (Aβ25-39, SEQ ID NO. 10), and/or KGAIIGLMVGGVVIA (Aβ28-42, SEQ ID NO. 11).

In at least one embodiment of the present disclosure, the stimulating in the method described herein comprises incubating the T cells with an amyloid peptide pool for a period of time. In some embodiments, the amyloid peptide pool comprises at least two (e.g., 2, 3, 4, 5, 6, 7, 8, 9, and 10) fragments selected from the group consisting of SEQ ID NOs. 2 to 11. In some embodiments, the period of time may be at least 3 hours, such as 4, 5, 6, 7, 8, 9, 10, 11, and 12 hours.

In at least one embodiment of the present disclosure, the evaluating in the method described herein comprises measuring a level of a T cell response biomarker from the stimulated T cells, wherein the biomarker is at least one selected from the group consisting of CD107a, IFNγ, IL-2, TNFα, and any combinations thereof. In some embodiments, the evaluating further comprises comparing the measured level of the biomarker to a reference level, and wherein a greater level of the biomarker as compared to the reference level is indicative of a higher likelihood that the subject is afflicted with or at risk of MCI. In some embodiments, the evaluating comprises measuring levels of at least two of CD107a, IFNγ, IL-2, and TNFα from the stimulated CD4+ T cells.

In at least one embodiment of the present disclosure, a kit for diagnosing a subject having or at risk of having MCI is also provided. The kit of the present disclosure comprises the amyloid β peptide or the fragment thereof as described above, and at least one reagent that is specific to at least one T cell response biomarker. In some embodiments, the T cell response biomarker is selected from the group consisting of CD107a, IFNγ, IL-2, and TNFα. In some embodiments, the kit further comprises an instruction for use in accordance with the above method.

In the present disclosure, with the evaluation of magnitude of an amyloid-specific T cell response, the method and the kit described herein may be used to efficiently identify a subject with risk for developing MCI. The method for such identification provided herein may be useful for prediction of the development of an amyloid-related neurodegenerative disease at stages where it is not clinically expressed or in the early stages of its clinical expression. Such disease may be, for example, Alzheimer's disease, Parkinson's disease, amyotrophic lateral sclerosis (ALS), multiple sclerosis (MS), cerebral amyloid angiopathy, inflammatory cerebral amyloid angiopathy or cerebral amyloidoma. In some embodiments, the identification provided herein may be utilized to monitor a response, a side effect, or a combination thereof of the amyloid β peptide, the fragment thereof or an aggregate-related treatment, predict an efficacy of the amyloid β peptide, the fragment thereof or an aggregate-related treatment, and/or guide a therapeutic decision of the amyloid β peptide, the fragment thereof or an aggregate-related treatment, such as monoclonal antibodies therapy. In some embodiments, the side effect is selected from the group consisting of weakness, headache, fever, chills, nausea, vomiting, diarrhea, rashes, low blood pressure, and any combination thereof.

In some embodiments, the method can be used to monitor at least one amyloid-related disease selected from the group consisting of Alzheimer disease, Parkinson's disease, amyotrophic lateral sclerosis, multiple sclerosis, cerebral amyloid angiopathy, inflammatory cerebral amyloid angiopathy and cerebral amyloidoma. In some embodiments, the method can be used to evaluate a T cell response induced by the amyloid β peptide or the fragment thereof.

BRIEF DESCRIPTION OF THE DRAWINGS

The present disclosure can be more fully understood by reading the following descriptions of the embodiments, with reference made to the accompanying drawings.

DETAILED DESCRIPTION OF THE EMBODIMENTS

Figure 1A:
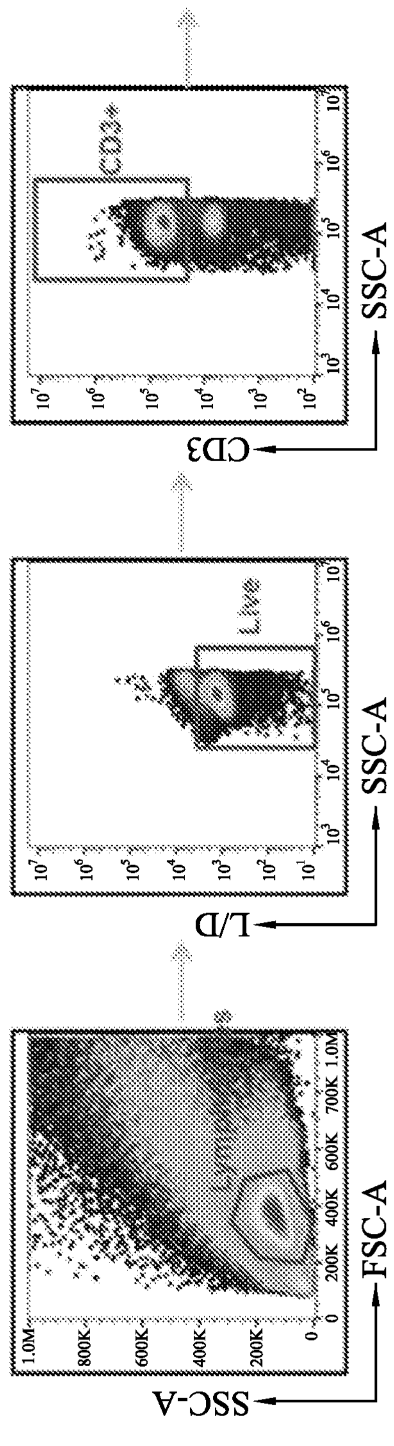
FIGS. 1A and 1B illustrate the representative flow cytometry plots of amyloid β peptide pool-specific T cell response (FIG. 1A) or full-length amyloid β-specific T cell response (FIG. 1B). SSC-A: side scatter area; FSC-A: forward scatter area; L/D: Live/Dead; IFNg: interferon-γ (IFNγ); TNFa: tumor necrosis factor-α (TNFα).
Figure 1A:
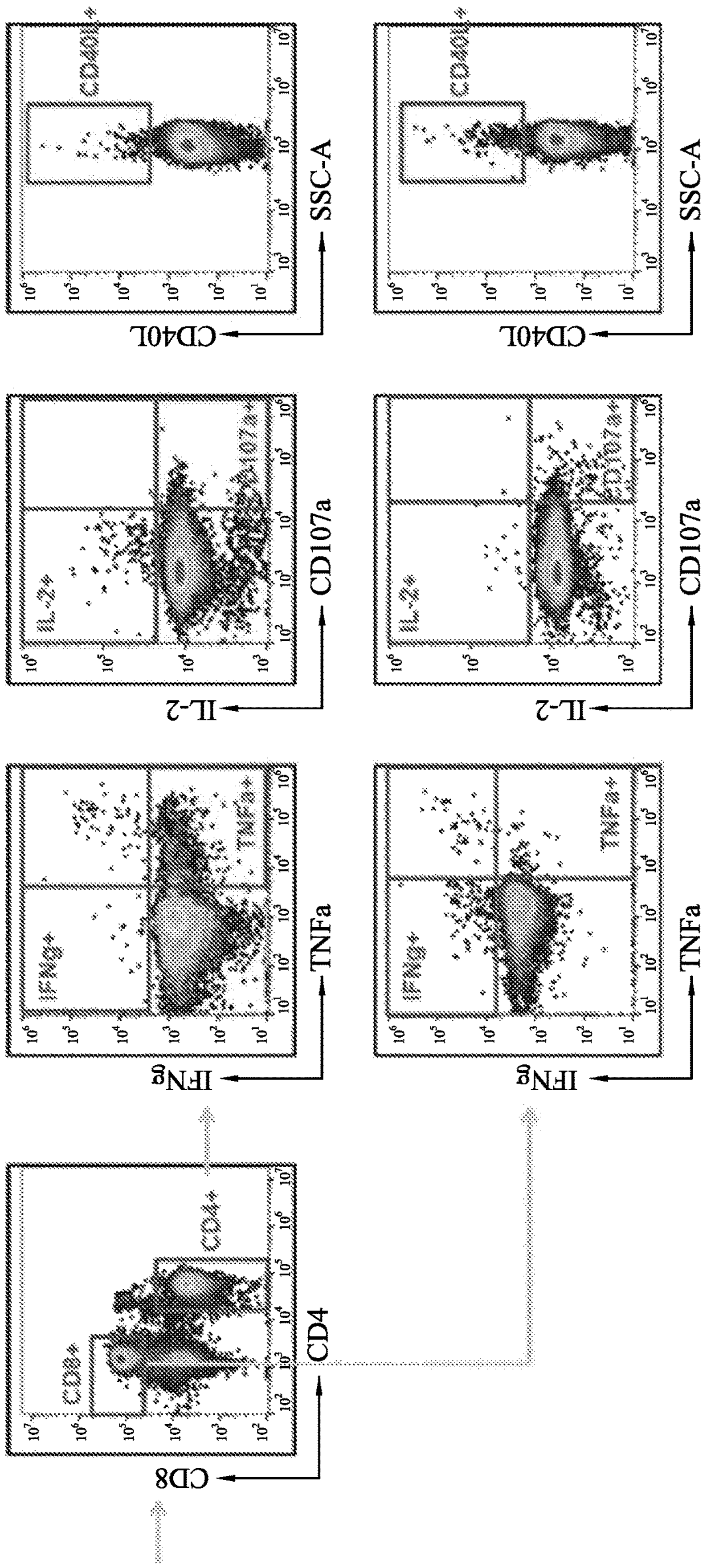

The following examples are used to exemplify the present disclosure. A person of ordinary skill in the art can understand the other advantages of the present disclosure, based on the specification of the present disclosure. The present disclosure can also be implemented or applied as described in different examples. It is possible to modify and/or alter the following examples for carrying out this disclosure without contravening its scope for different aspects and applications.

It is noted that, as used in this disclosure, the singular forms "a," "an," and "the" include plural referents unless expressly and unequivocally limited to one referent. The term "or" is used interchangeably with the term "and/or" unless the context clearly indicates otherwise. For example, when separating items in a list, "or" or "and/or"shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

As used herein, the term "essentially" refers to at least 50%, 55%, 60%, 65%, 70%, 75%, 80%, 85%, 90%, 95%, 96%, 97% or greater of the said feature. For example, the term "consisting essentially of" used herein may indicate a peptide consisting of at least 50%, 55%, 60%, 65%, 70%, 75%, 80%, 85%, 90%, 95%, 96%, 97% or greater of the amino acids of the referential sequence.

As used herein, the term "comprising" or "comprises" is used in reference to compositions, methods, and respective component(s) thereof, which are included in the present disclosure, yet open to the inclusion of unspecified elements. For example, a composition, mixture, process or method that comprises a list of elements or actions is not necessarily limited to only those elements or actions, but may include other elements or actions not expressly listed, or inherent to such composition, mixture, process, or method.

As used herein, the phrases "at least one" and "one or more" may have the same meaning and include one, two, three, or more. For example, the phrase "at least one," in reference to a list of one or more elements, should be understood to mean at least one element selected from any one or more of the elements in the list of elements, but not necessarily including at least one of each and every element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, the term "about" generally means within 10%, 5%, 1%, or 0.5% of a given value or range. Alternatively, the term "about" means within an acceptable standard error of the mean when considered by one of ordinary skill in the art. Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about."

As used herein, the terms "subject," "individual" and "patient" may be interchangeable and refer to an animal, e.g., a mammal. For example, the term "subject" may refer to both the male and female gender unless one gender is specifically indicated. Further, the term "patient" may refer to a "subject" who is suspected to be, or afflicted with a disease or condition. In some embodiments, the subject to be tested with the method of the present disclosure may be a human, a domestic animal (e.g., a dog, a cat, or the like), a farm animal (e.g., a cow, a sheep, a pig, a horse, or the like) or a laboratory animal (e.g., a monkey, a rodent, a murine, a rabbit, a guinea pig, or the like).

As used herein, the term "biological sample" refers to any sample including: tissue samples (such as tissue sections and needle biopsies of a tissue); cell samples (e.g., cytological smears (such as Pap or blood smears) or samples of cells obtained by microdissection); or cell fractions, fragments or organelles (such as those obtained by lysing cells and separating the components thereof by centrifugation or otherwise). Other examples of biological samples include brain tissue, whole blood, serum, plasma, urine, sputum, saliva, cerebrospinal fluid, sweat, stool extract, synovial fluid, tears, peritoneal fluid, or any combination thereof.

As used herein, the term "diagnosing," "diagnostic," and "diagnosis" refer to methods by which a skilled artisan may estimate and/or determine the probability ("a likelihood") of whether or not a subject is suffering from a given disease or condition. That such a diagnosis is "determined" is not meant to imply that the diagnosis is 100% accurate. Many biomarkers are indicative of multiple conditions. A skilled clinician does not use biomarker results in an informational vacuum, but rather test results are used together with other clinical indicia to arrive at a diagnosis. Thus, a measured biomarker level on one side of a predetermined diagnostic threshold may indicate a greater likelihood of the occurrence of a disease in the subject relative to a measured level on the other side of the predetermined diagnostic threshold.

As used herein, the term "development" or "progression" of a disease refers to initial manifestations and/or ensuing progression of the disease. Development of the disease may be detectable and assessed using standard clinical techniques as well known in the art. However, development also refers to progression that may be undetectable. The term "development" includes occurrence, recurrence, and onset of a disease, condition or disorder. As used herein, the term "onset" or "occurrence" of a target disease, condition or disorder includes initial onset and/or recurrence thereof.

In at least one embodiment, the present disclosure is directed to a method for diagnosing a subject having or at risk of having mild cognitive impairment (MCI), comprising stimulating T cells in a biological sample obtained from the subject with an amyloid β peptide or a fragment thereof, and evaluating a magnitude of a T cell response toward the amyloid β peptide or the fragment thereof.

In at least one embodiment of the present disclosure, the evaluating comprises measuring a level of a T cell response biomarker from the stimulated T cells, such as CD4+ T cells. In some embodiments, the evaluating further comprises comparing the measured level of the biomarker to a reference level, wherein a greater level of the biomarker as compared to the reference level is indicative of a higher likelihood that the subject is afflicted with or at risk of MCI.

As used herein, a "reference level" may be an absolute value, a relative value, a range of values, an average value, a median value, a mean value, a statistic value, a cut-off or discriminating value, or a value as compared to a particular control or baseline value. The reference level may be based on an individual sample value, such as a value obtained from a sample from a subject other than the individual tested or from a "normal" individual that is an individual identified as having a healthy status or an individual not diagnosed with MCI.

In at least one embodiment of the present disclosure, the T cells to be stimulated with the amyloid β peptide or the fragment thereof may be present in peripheral blood mononuclear cells (PBMCs) of the subject. In some embodiments, the method described herein may further comprise providing a biological sample (such as a fluid biological sample or a tissue sample) of the subject and isolating the PBMCs from the biological sample.

In at least one embodiment of the present disclosure, the method described herein may further comprise performing an additional assay for diagnosis of MCI, thereby increasing the diagnostic accuracy. The additional assay for diagnosis of MCI may be well known in the art. For example, the clinical criteria used for diagnosis of MCI include (1) memory complaints corroborated by an informant; (2) objective memory impairment beyond that expected for age and education; (3) normal general cognitive function; (4) intact activities of daily living; and (5) the subject failing to meet criteria for dementia.

In at least one embodiment, the present disclosure is also directed to a kit for diagnosing a subject having or at risk of having MCI. As used herein, the term "kit" includes, but is not limited to, at least one reagent for detecting, identifying, and/or analyzing a biological sample from a subject, and a legend providing instructions to the user on how to use the kit. The kit provided herein may be in suitable packaging, including, but not limited to, vials, bottles, jars, flexible packaging, and the like. Also contemplated are packages for use in combination with a medical device which is applicable and well known in this field with no limitation.

In at least one embodiment of the present disclosure, the kit comprises an amyloid β peptide or a fragment thereof, and at least one reagent that is specific to at least one T cell response biomarker, such as cluster of differentiation 107a (CD107a), interferon-γ (IFNγ), interleukin 2 (IL-2), and tumor necrosis factor-α (TNFα). In some embodiments, the reagent can be an antibody that specifically binds to the corresponding biomarker thereof based on antigen-antibody interaction, such as an anti-CD107a antibody, an anti-IL-2 antibody, an anti-TNFα antibody, and an anti-IFNγ antibody.

In at least one embodiment, the kit of the present application may comprise instructions for use in accordance with any of the methods described herein. The included instructions may comprise a description of incubating T cells with the amyloid β peptide or the fragment thereof. The kit may further comprise a description of evaluating the magnitude of an amyloid-specific T cell response by measuring the level of the T cell response biomarker. In some embodiments, the reagent contained in the kit is detectable for measuring the level of the T cell response biomarker. The biomarkers labeled with the detectable reagent may be quantitated by using assays including, but not limited to, flow cytometry, magnetic-activated cell sorting (MACS) and enzyme-linked immunospot (ELISPOT) assay.

As used herein, the phrase "specifically binds" to a target refers to a binding reaction that is determinative of the presence of a molecule in the presence of a heterogeneous population of other biologics. Therefore, under designated immunoassay conditions, a specified molecule binds preferentially to a particular target and does not bind in a significant amount to other biologics present in the sample.

Many examples have been used to illustrate the present disclosure. The examples below should not be taken as a limit to the scope of the present disclosure.

EXAMPLES

Example 1

Sample Processing and PBMCs Isolation

For blood sampling, human subjects were recruited from Far Eastern Memorial Hospital (FEMH) in this study. The study was approved by the FEMH's institutional ethical committee (Case No. FEMH 105147-F) and written informed consent were acquired from all participants. Detailed information on study participants was listed in Table 1 below.

TABLE 1

Demographic data of the human subjects

| Characteristics | MCI (N = 69) | Normal (N = 69) | P-value |
|---|---|---|---|
| Age, years, mean (SD) | 72.1 (4.9) | 71.8 (5.5) | 0.79 |
| Female, no. (%) | 38 (55.0) | 40 (58.0) | 0.73 |
| Education, years, mean (SD) | 5.4 (3.1) | 6.7 (3.6) | 0.029 |
| Married, no. (%) | 57 (83.0) | 51 (74.0) | 0.22 |
| Never smoking, no. (%) | 51 (74.0) | 51 (74.0) | 0.73 |
| Hypertension, no. (%) | 36 (52.0) | 35 (51.0) | 0.86 |
| Cardiovascular diseases, no. (%) | 16 (24.0) | 10 (15.0) | 0.19 |
| BMI, kg/$m^2$, mean (SD) | 24.9 (3.0) | 25.4 (3.3) | 0.28 |
| GDS >5, no. (%) | 13 (19.0) | 8 (12.0) | 0.24 |

TABLE 1-continued

Demographic data of the human subjects

| Characteristics | MCI (N = 69) | Normal (N = 69) | P-value |
|---|---|---|---|
| MMSE, mean (SD) | 24.9 (3.0) | 25.4 (3.3) | <0.001 |
| APOE4, no. (%) | 14 (20.0) | 10 (14.0) | 0.37 |
| Amyloid pool total response, mean (SD) | 0.9 (0.7) | 0.5 (0.6) | <0.001 |
| Amyloid full-length total response, mean (SD) | 0.8 (0.7) | 0.3 (0.3) | <0.001 |

SD: standard deviation;
BMI: body mass index;
GDS: geriatric depression scale;
MMSE: mini-mental state examination;
APOE4: apolipoprotein E4.

On the day of blood sampling, peripheral blood mononuclear cells (PBMCs) were isolated by Ficoll-Paque PLUS gradient centrifugation following the manufacturer's protocol (GE Healthcare) and used in the subsequent experiment.

Example 2

T Cell Stimulation and Quantification of a T Cell Response Against Amyloid

The use of protein-spanning mixtures of overlapping peptides was efficient for immunostimulation of T-lymphocytes and diagnostic applications. In this disclosure, the overlapping 15mer peptides derived from the full-length amyloid β protein (Aβ1-42) were created and used for T cell stimulation. The cytomegalovirus (CMV) pp65 protein peptide pool (JPT Peptide Technologies, Germany) and chemical phorbol myristate acetate (PMA)/ionomycin were used as positive controls for PBMC stimulation.

The amino acid sequence of the full-length amyloid β protein (Aβ1-42) from JPT Peptide Technologies were DAEFRHDSGYEVHHQKLVFFGEDVGSNK-GAIIGLMVGGVVIA (SEQ ID NO. 1). The peptide pool composed of 10 sequences created based on 15mer amino acid length with sequential 3 amino acid shifts of the full-length amyloid β protein (Aβ1-42) included: DAE-FRHDSGYEVHHQ (Aβ1-15, SEQ ID NO. 2), FRHDSGYEVHHQKLV (Aβ4-18, SEQ ID NO. 3), DSGYEVHHQKLVFFG (Aβ7-21, SEQ ID NO. 4), YEVHHQKLVFFGEDV (Aβ10-24, SEQ ID NO. 5), HHQKLVFFGEDVGSN (Aβ13-27, SEQ ID NO. 6), KLVFFGEDVGSNKGA (Aβ16-30, SEQ ID NO. 7), FFGEDVGSNKGAIIG (Aβ19-33, SEQ ID NO. 8), EDVG-SNKGAIIGLMV (Aβ22-36, SEQ ID NO. 9), GSNK-GAIIGLMVGGV (Aβ25-39, SEQ ID NO. 10) and KGAIIGLMVGGVVIA (Aβ28-42, SEQ ID NO. 11).

The full-length amyloid β protein as well as the amyloid peptide pool and control CMV peptide pool were used for PBMC cell stimulation (1 mg/mL per peptide) along with co-stimulation of anti-CD28/CD49d, anti-CD107a, Golgi Stop (containing monensin, BD Biosciences) and GolgiPlug (containing brefeldin A, BD Biosciences) for six hours at 37 °C. Subsequently, cells were stained with anti-CD3, anti-CD8, anti-CD4 and Live/Dead Cell Viability Assay Kit (Invitrogen) for 20 minutes before fixation with Cytofix/Cytoperm buffer (BD Biosciences). Cells were fixed, washed, and stained with anti-CD40L, anti-IL-2, anti-TNFα, and anti-IFNγ. Results were acquired using a multicolor flow cytometer (Beckman Coulter Cytoflex) at the Far Eastern Memorial Hospital Core Lab. Flow cytometry results were analyzed using FlowJo (Tree Star).

Figure 1B:
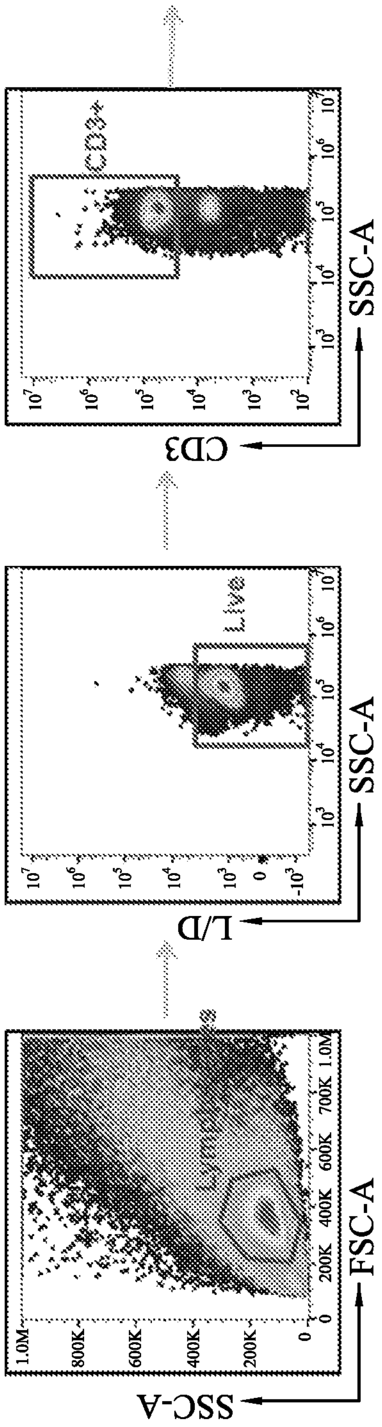
Figure 1B:
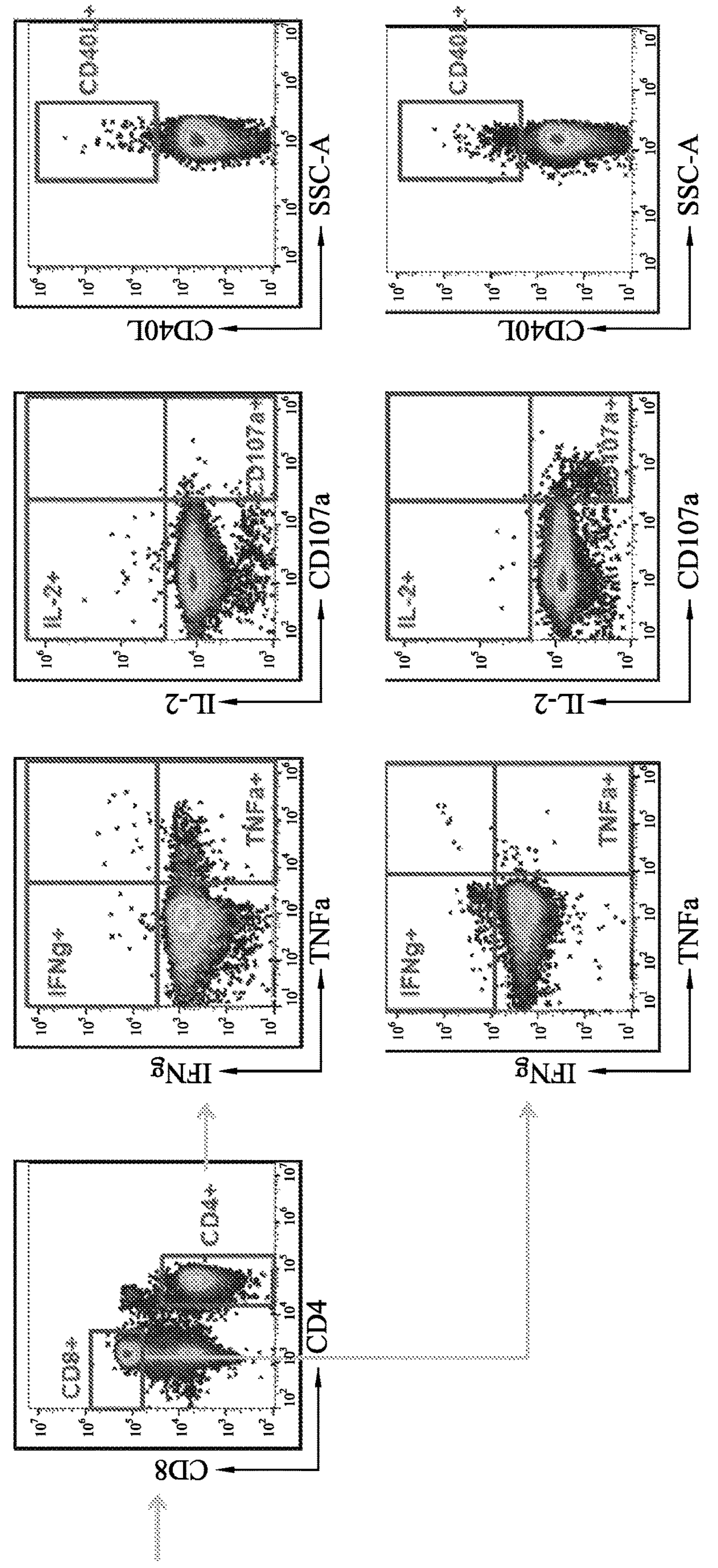
Figure 2A:
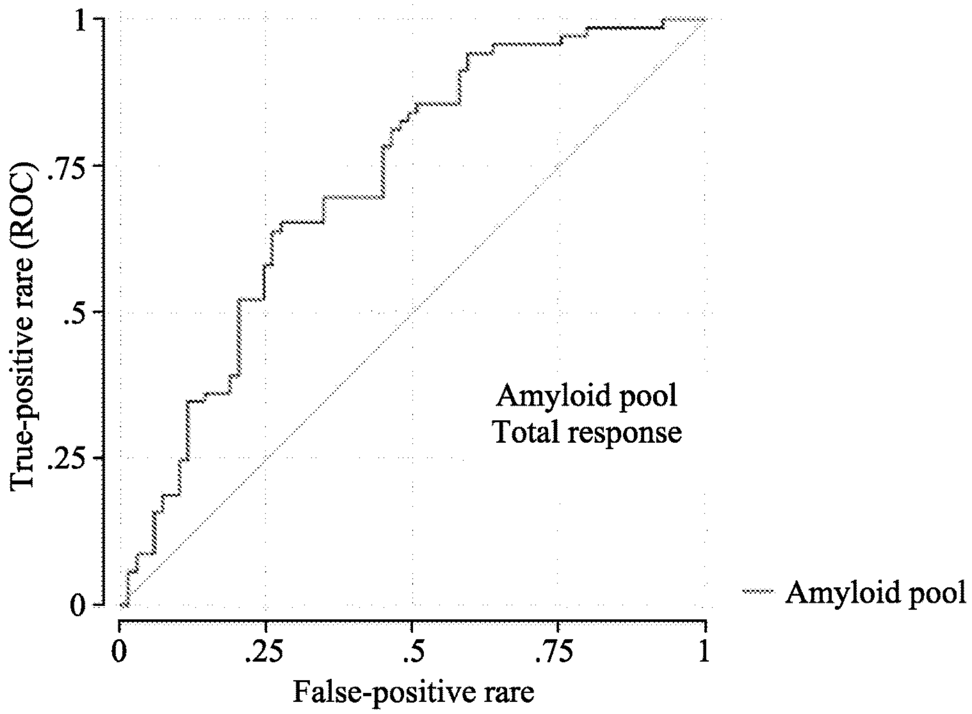
FIGS. 2A to 2F and 3A to 3F illustrate the results of operating characteristic curve (ROC) analyses of T cell response biomarkers for amyloid β peptide pool response (FIGS. 2A to 2F) or amyloid β full-length peptide response (FIGS. 3A to 3F).
Figure 2B:
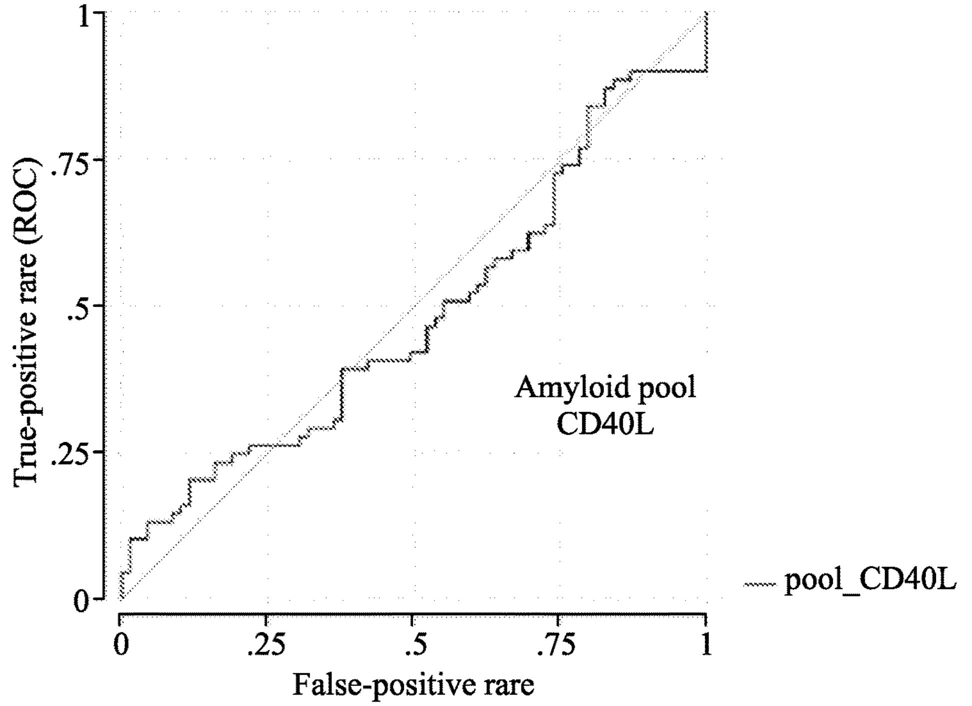
Figure 2C:
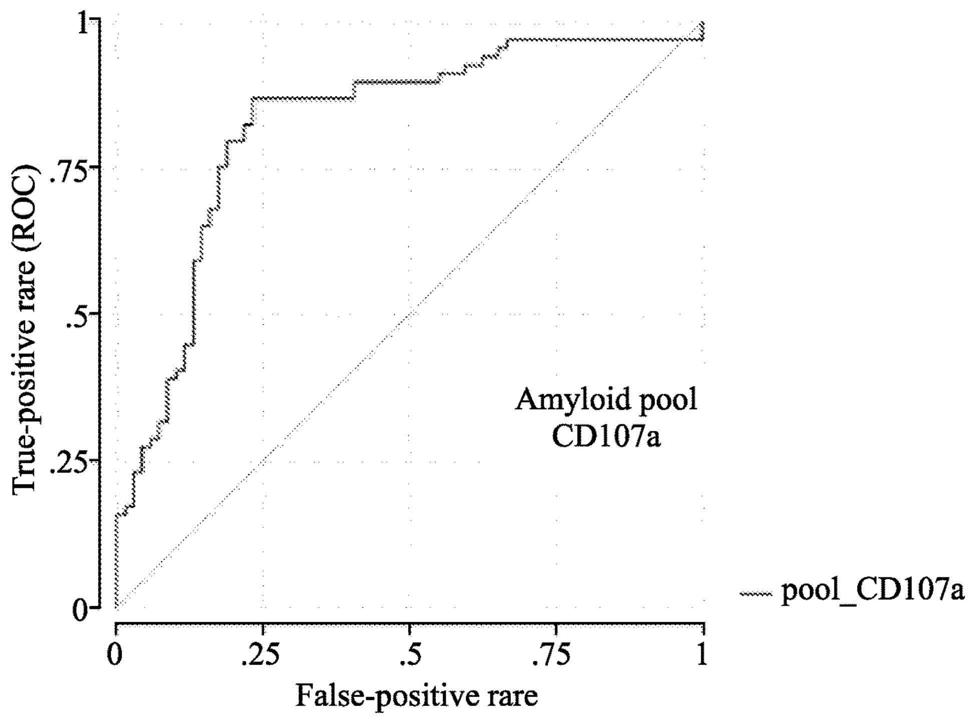
Figure 2D:
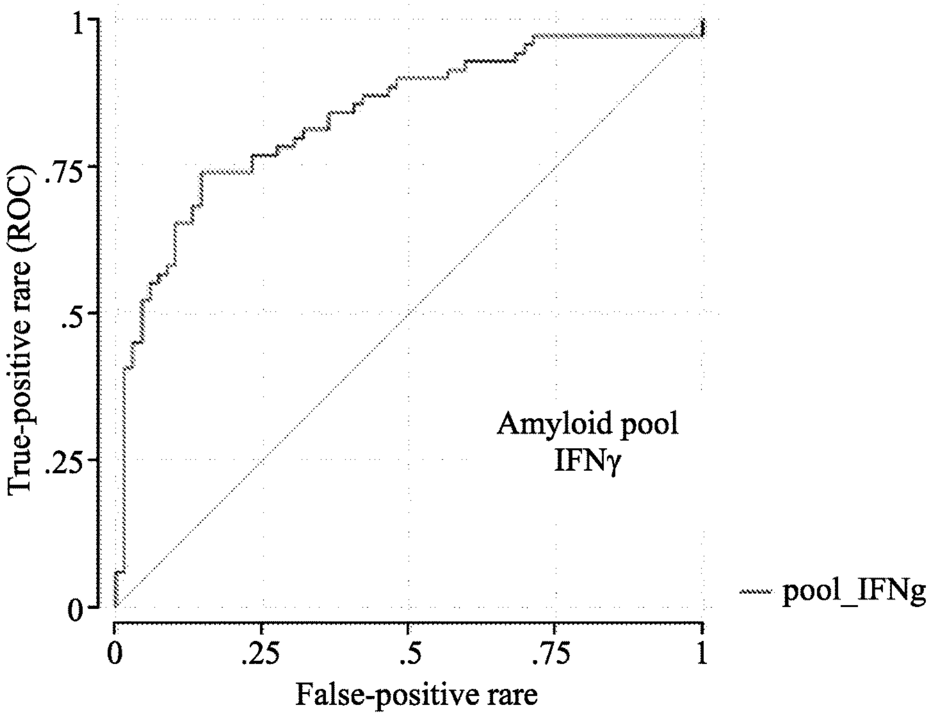
Figure 2E:
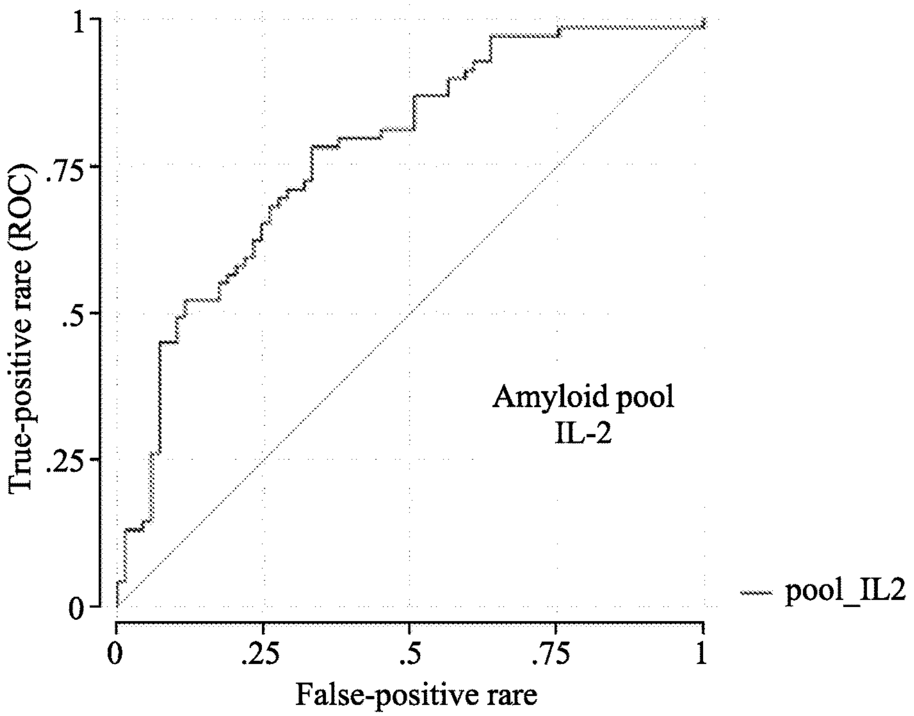
Figure 2F:
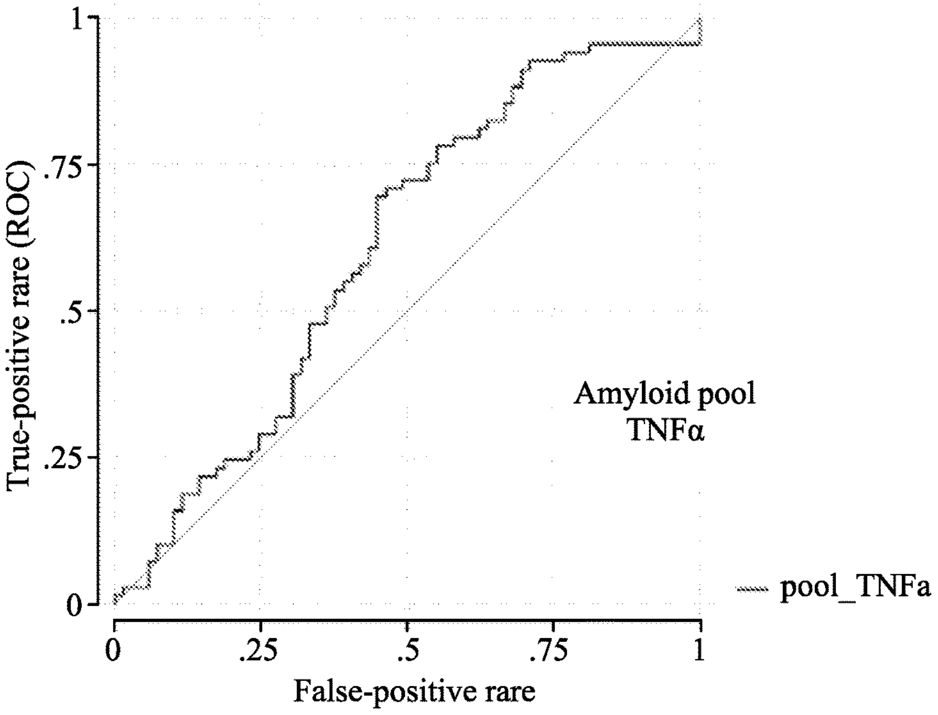
Figure 3A:
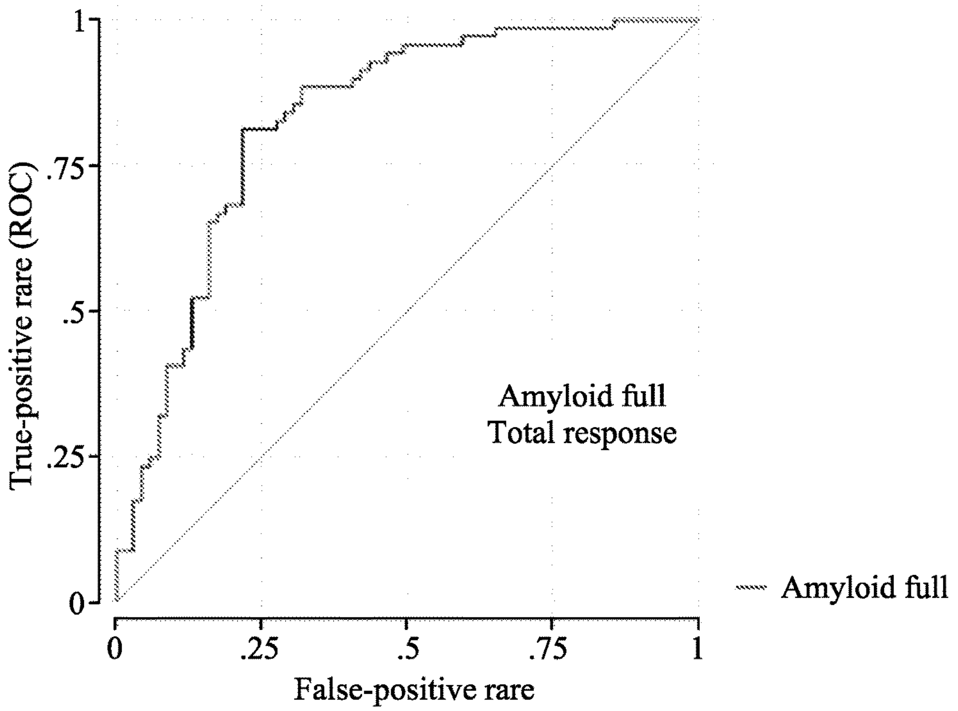
Figure 3B:
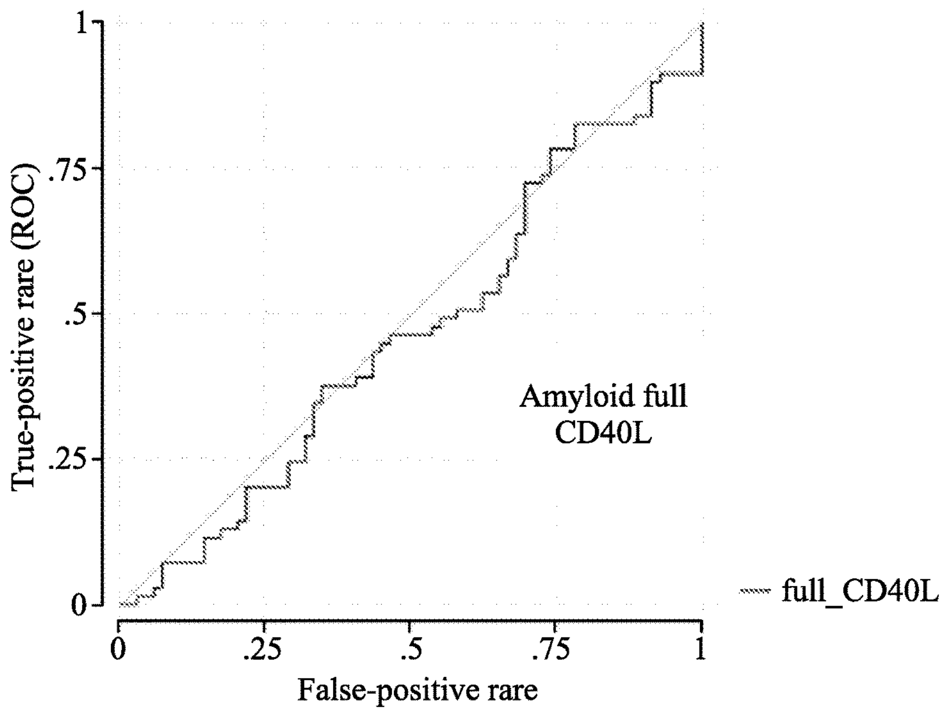
Figure 3C:
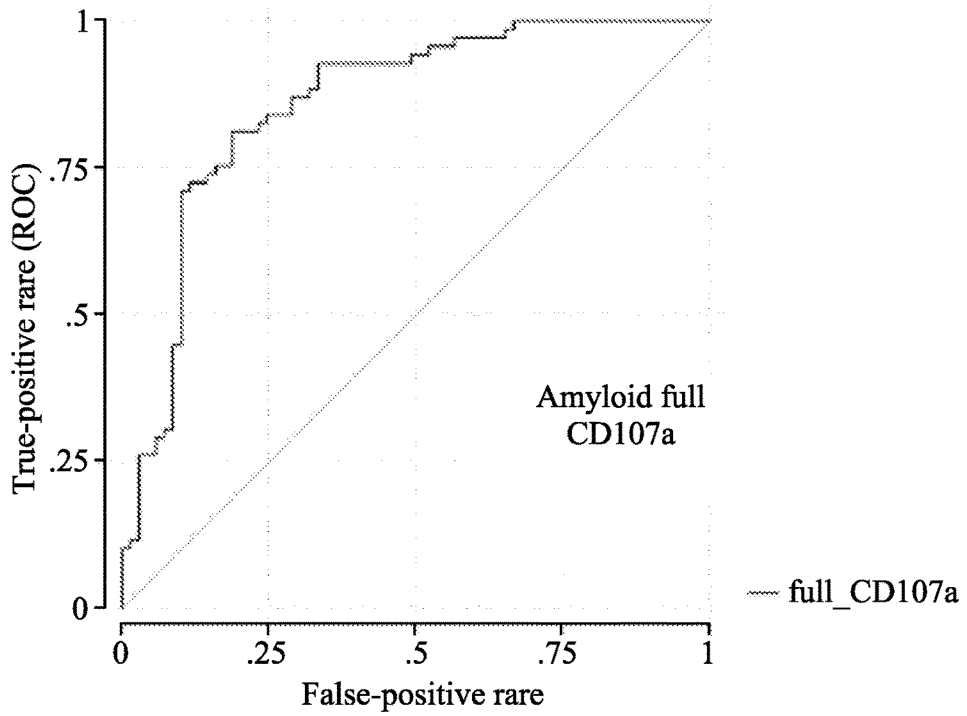
Figure 3D:
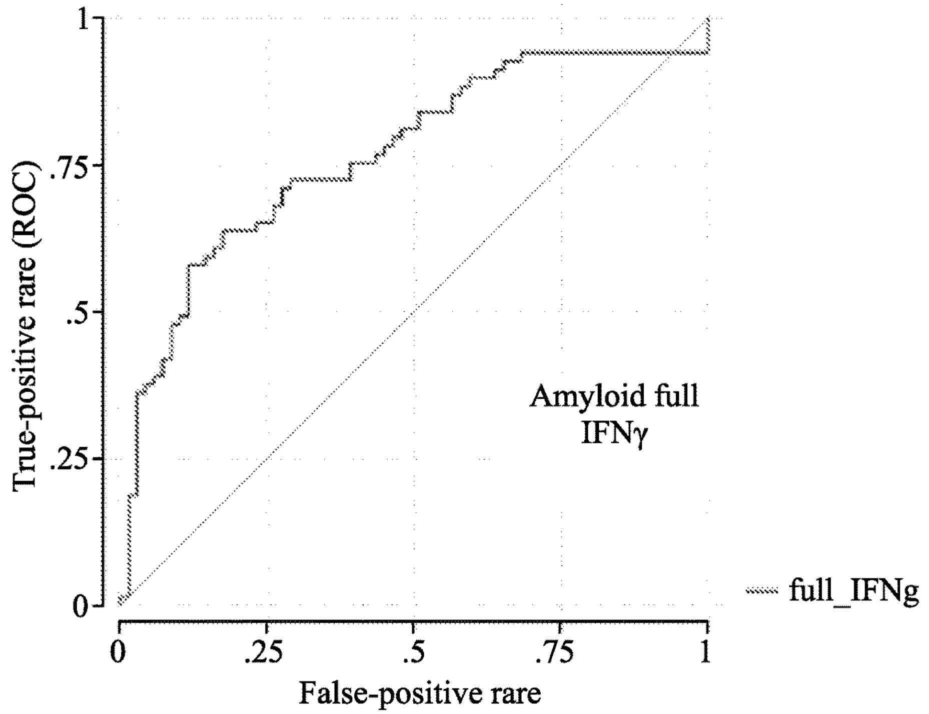
Figure 3E:
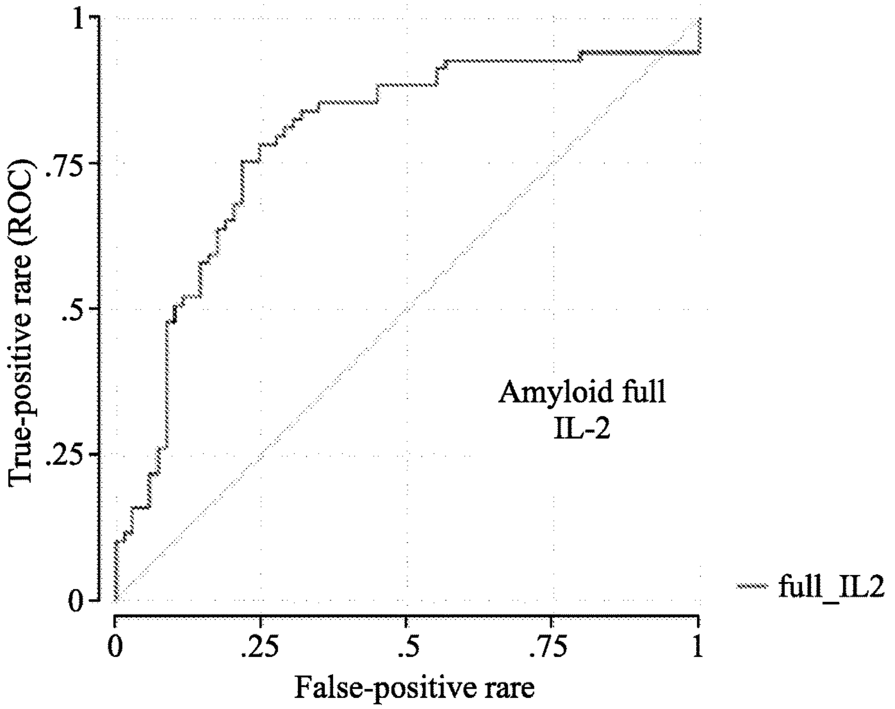
Figure 3F:
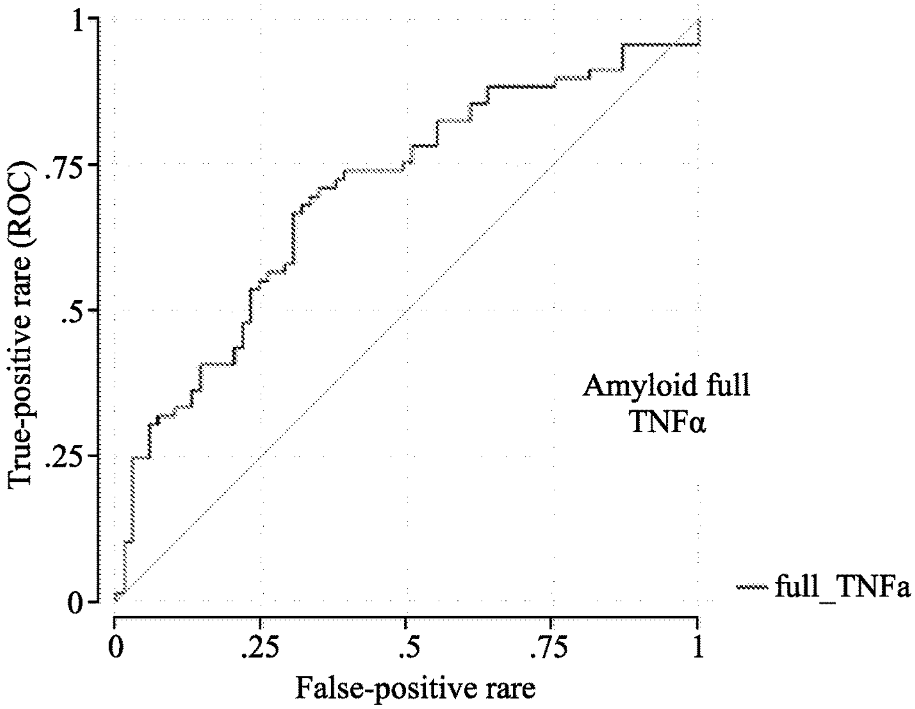

After gated on live CD3+ cells, CD4+ and CD8+ cells were analyzed separately for cytokine expression in response toward each stimulation. A combinatorial gating strategy based on the gates of each effector function was further analyzed for co-expression pattern using the FlowJo Boolean gate platform to derive the statistics of combinatorial function expression pattern. Each single function and total functional response of T cells against each stimulation was derived and compared. The representative images of T cell cytokine production in response toward amyloid protein were shown in FIGS. 1A and 1B. The representative images of T cell cytokine production in response toward amyloid peptide pool were shown in FIG. 1A. The representative images of T cell cytokine production in response toward amyloid full-length peptide were shown in FIG. 1B.

Magnitudes of PBMC CD4+ T cell response toward amyloid β peptide pool and amyloid β full-length peptide were tested for their sensitivity and specificity for distinguishing MCI from normal. Correctly classified participants, sensitivity, and specificity were calculated using the cut-off that produced the highest index from Liu's method for MCI versus normal. Total response was enumerated as the percentage of T cells among total CD4+ T cells responding toward the amyloid β peptide pool and amyloid β full-length peptide stimulation with at least one measured biomarker (i.e., CD40L, CD107a, IFNγ, IL-2 or TNFα).

The area under the receiver operating characteristic curve (ROC) was used to examine the discriminative performance of the biomarkers. Confidence intervals (CI) for areas under curve (AUCs) were calculated based on 2,000 bootstrap samples using the non-parametric method. The cut-offs for amyloid pool and amyloid full-length peptide responses were established at the highest product of sensitivity and specificity to discriminate between MCI and age-matched normal in each ROC analysis (Liu's method). The results of ROC analyses were shown in Tables 2 and 3 below and FIGS. 2A to 2F and 3A to 3F.

TABLE 2

ROC analyses of T cell response biomarkers for amyloid β peptide pool response

| Biomarker (% CD4 + T cell) | AUC (95% CI) | Cut-off | Correctly classified participants | Sensitivity | Specificity |
|---|---|---|---|---|---|
| Total response | 0.72 (0.63-0.8) | 0.53 | 0.69 | 0.65 | 0.72 |
| CD40L | 0.48 (0.38-0.57) | 0.1 | 0.51 | 0.39 | 0.62 |
| CD107a | 0.83 (0.75-0.89) | 0.036 | 0.82 | 0.87 | 0.77 |
| IFNγ | 0.84 (0.76-0.9) | 0.062 | 0.80 | 0.74 | 0.86 |
| IL-2 | 0.77 (0.69-0.85) | 0.0485 | 0.72 | 0.78 | 0.67 |
| TNFα | 0.61 (0.51-0.7) | 0.081 | 0.62 | 0.70 | 0.55 |

TABLE 3

ROC analyses of T cell response biomarkers for amyloid β full-length peptide response

| Biomarker (% CD4 + T cell) | AUC (95% CI) | Cut-off | Correctly classified participants | Sensitivity | Specificity |
|---|---|---|---|---|---|
| Total response | 0.83 (0.75-0.89) | 0.314 | 0.8 | 0.81 | 0.78 |
| CD40L | 0.46 (0.37-0.56) | 0.056 | 0.5 | 0.46 | 0.54 |
| CD107a | 0.86 (0.79-0.91) | 0.06 | 0.81 | 0.81 | 0.81 |

TABLE 3-continued

ROC analyses of T cell response biomarkers for amyloid β full-length peptide response

| Biomarker (% CD4 + T cell) | AUC (95% CI) | Cut-off | Correctly classified participants | Sensitivity | Specificity |
|---|---|---|---|---|---|
| IFNγ | 0.77 (0.68-0.84) | 0.064 | 0.73 | 0.64 | 0.83 |
| IL-2 | 0.79 (0.7-0.86) | A single cut-off cannot be determined because there are multiple cut-offs with the same sensitivity and specificity | | | |
| TNFα | 0.7 (0.61-0.79) | 0.048 | 0.68 | 0.68 | 0.68 |

From the above, it is found that CD4+ T cell responses toward amyloid β full-length peptide as well as amyloid β peptide pool can be used to distinguish elderly MCI and normal elderly. The method provided herein is based on stimulation of PBMCs and measurements of a cytokine effector response in stimulated T cells by multicolor flow cytometry, and thus is easier to be standardized when compared to proliferation assays. Because blood T cell responses toward amyloid peptide are rare events (with less than 0.1% of T cells among CD4+ cells), the multi-marker method provided herein increases the absolute value of measurements to more than 0.1% and shows persistent ability to distinguish MCI from normal. Accordingly, the method of the present disclosure can be utilized to categorize elderly individuals with risk for developing MCI and used to investigate its predictive power for the development of any amyloid-related neurodegenerative diseases.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

All references and publications cited and discussed herein are hereby incorporated by reference in their entirety and to the same extent as if each reference or publication was individually incorporated by reference.

REFERENCE

[1] Ferri C P, Prince M, Brayne C, et al. Global prevalence of dementia: a Delphi consensus study. *Lancet* 2005; 366(9503):2112-7.

[2] Morris J C. Early-stage and preclinical Alzheimer disease. *Alzheimer Disease and Associated Disorders* 2005; 19(3): 163-5.

[3] Gauthier S, Reisberg B, Zaudig M, et al. Mild cognitive impairment. *Lancet* 2006; 367(9518):1262-70.

[4] Petersen R C. Mild cognitive impairment: current research and clinical implications. *Seminars in Neurology* 2007; 27(1):22-31.

[5] Petersen R C, Smith G E, Waring S C, et al. Mild cognitive impairment: clinical characterization and outcome. *Archives of Neurology* 1999; 56(3):303-8.

[6] Masters C L, Beyreuther K. The neuropathology of Alzheimer's disease in the year 2005. In: Beal M F, Lang A E, Ludolph A C, eds. Neurodegenerative Diseases: Neurobiology, Pathogenesis and Therapeutics. Cambridge: Cambridge University Press 2005.

[7] Rabinovici G D, Jagust W J. Amyloid imaging in aging and dementia: testing the amyloid hypothesis in vivo. *Behavioural Neurology* 2009; 21(1): 117-28.

[8] Small G W, Kepe V, Ercoli L M, et al. PET of brain amyloid and tau in mild cognitive impairment. The *New England Journal of Medicine* 2006; 355(25): 2652-6.

[9] Villemagne V L, Chetelat G. Neuroimaging biomarkers in Alzheimer's disease and other dementias. *Ageing Research Reviews* 2016; 30:4-16.

[10] Pike K E, Savage G, Villemagne V L, et al. Beta-amyloid imaging and memory in non-demented individuals: evidence for preclinical Alzheimer's disease. *Brain* 2007; 130(Pt 11):2837-44.

[11] Ong K, Villemagne V L, Bahar-Fuchs A, et al. $^{18}$F-florbetaben Aβ imaging in mild cognitive impairment. *Alzheimer's Research and Therapy* 2013; 5(1):4.

[12] Ma Y, Zhang S, Li J, et al. Predictive accuracy of amyloid imaging for progression from mild cognitive impairment to Alzheimer disease with different lengths of follow-up: a meta-analysis. *Medicine* (*Baltimore*) 2014; 93(27):e150.

What is claimed is:

1. A method for diagnosing a subject having or at risk of having mild cognitive impairment (MCI), comprising:

obtaining from the subject a tissue sample or a fluid biological sample, obtaining from the tissue sample or the fluid biological sample peripheral blood mononuclear cells (PBMCs), stimulating the PBMCs with an amyloid β peptide or a fragment thereof and one or more co-stimulant comprising anti-CD28/CD49d antibody, anti-CD107a antibody, monensin, and brefeldin A; and gating the stimulated PBMCs for live CD3+ cells to separate stimulated T cells from the stimulated PBMCs, evaluating a magnitude of a T cell response toward the amyloid β peptide or the fragment thereof and the one or more co-stimulant by measuring a level of a biomarker from the stimulated T cells; and comparing the measured level of the biomarker to a reference level;

wherein a greater level of the biomarker as compared to the reference level is indicative of a higher likelihood that the subject is afflicted with or at risk of MCI;

wherein the amyloid β peptide comprises an amino acid sequence represented by SEQ ID NO. 1 or SEQ ID NO. 12; and wherein the biomarker is at least one selected from the group consisting of CD107a, IFNγ, IL-2, TNFα, and any combinations thereof.

2. The method according to claim 1, wherein the evaluating comprises measuring levels of at least two of CD107a, IFNγ, IL-2, and TNFα from the stimulated T cells.

3. The method according to claim 1, wherein the tissue sample or the fluid biological sample is obtained from blood, plasma, serum, urine, sputum, saliva, cerebrospinal fluid, sweat, stool extract, tears, peritoneal fluid or brain of the subject.

4. The method according to claim 1, wherein the fragment of the amyloid β peptide comprises at least nine consecutive amino acids of an amino acid sequence represented by SEQ ID NO. 1 or SEQ ID NO. 12.

5. The method according to claim 1, wherein the fragment of the amyloid β peptide comprises an amino acid sequence represented by any one of SEQ ID NOs. 2 to 11.

6. The method according to claim 1, wherein the stimulating comprises incubating the PBMCs with the amyloid β peptide or the fragment thereof for at least 3 hours.

7. The method according to claim 1, wherein the subject is a mammal.

8. The method according to claim 7, wherein the mammal is selected from the group consisting of a human, a dog, a cat, a cow, a sheep, a pig, a horse, a monkey, a rodent, a murine, a rabbit, and a guinea pig.

9. A kit for diagnosing a subject having or at risk of having mild cognitive impairment (MCI) to be used for the method according to claim 1, comprising:

an amyloid β peptide or a fragment thereof;

one or more co-stimulant comprising anti-CD28/CD49d antibody, anti-CD107a antibody, monensin, and brefeldin A; and at least one reagent selected from the group consisting of an anti-CD107a antibody, an anti-IL-2 antibody, an anti-TNFα antibody, and an anti-IFNγ antibody, wherein the amyloid β peptide has an amino acid sequence represented by SEQ ID NO. 1 or SEQ ID NO. 12.

10. The kit according to claim 9, wherein the fragment of the amyloid β peptide comprises at least 10 consecutive amino acids of an amino acid sequence represented by SEQ ID NO. 1 or SEQ ID NO. 12.

11. The kit according to claim 9, wherein the fragment of the amyloid β peptide has an amino acid sequence represented by any one of SEQ ID NOs. 2 to 11.

12. The kit according to claim 9, further comprising an instruction for use.

* * * * *